US010729316B2

(12) United States Patent
Thate et al.

(10) Patent No.: US 10,729,316 B2
(45) Date of Patent: Aug. 4, 2020

(54) REPROCESSING SURGICAL INSTRUMENTS, IN PARTICULAR ENDOSCOPES

(71) Applicant: OLYMPUS WINTER & IBE GMBH, Hamburg (DE)

(72) Inventors: Henning Thate, Hamburg (DE); Michael Lengsfeld, Hamburg (DE); Eugen Frick, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 16/288,198

(22) Filed: Feb. 28, 2019

(65) Prior Publication Data

US 2019/0191981 A1    Jun. 27, 2019

Related U.S. Application Data

(63) Continuation of application No. PCT/EP2017/070660, filed on Aug. 15, 2017.

(30) Foreign Application Priority Data

Aug. 31, 2016   (DE) .................. 10 2016 216 403

(51) Int. Cl.
*A61B 1/00*      (2006.01)
*A61B 1/12*      (2006.01)
(Continued)

(52) U.S. Cl.
CPC .......... *A61B 1/125* (2013.01); *A61B 1/00057* (2013.01); *A61B 1/123* (2013.01);
(Continued)

(58) Field of Classification Search
CPC .......... A61L 2202/17; A61L 2/18; A61L 2/24; A61L 2202/24; B08B 3/04; A61B 2090/701; A61B 1/125; A61B 1/00057
See application file for complete search history.

(56) References Cited

U.S. PATENT DOCUMENTS 6,408,682 B2 *  6/2002  Greszler ............ A61B 1/00057
                                                            73/40
8,973,449 B2    3/2015  Eschborn et al.
(Continued)

FOREIGN PATENT DOCUMENTS

DE        695 32 432 T2    12/2004
DE     20 2004 010 580 U1   12/2005
(Continued)

OTHER PUBLICATIONS

International Search Report dated Dec. 5, 2017 received in PCT/EP2017/070660.

*Primary Examiner* — Alexander Markoff
(74) *Attorney, Agent, or Firm* — Scully, Scott, Murphy & Presser, P.C.

(57) ABSTRACT

A method for reprocessing a surgical instrument in a reprocessing apparatus, where the surgical instrument has at least one channel to be cleaned. The method including: connecting the surgical instrument to a compressed air hose for supplying compressed air to the at least one channel; supplying drying air to the compressed air hose to leak test the surgical instrument using the drying air, the drying air having less moisture content than the compressed air; and subsequent to the supplying of the drying air, reprocessing the surgical instrument using at least one cleaning liquid.

8 Claims, 1 Drawing Sheet

(51) Int. Cl.
*A61L 2/18* (2006.01)
*A61L 2/24* (2006.01)
*B08B 3/04* (2006.01)
*A61B 90/70* (2016.01)

(52) U.S. Cl.
CPC .................. *A61L 2/18* (2013.01); *A61L 2/24* (2013.01); *B08B 3/04* (2013.01); *A61B 2090/701* (2016.02); *A61L 2202/17* (2013.01); *A61L 2202/24* (2013.01)

(56) References Cited

U.S. PATENT DOCUMENTS

| | | | |
|---|---|---|---|
| 2006/0252991 A1* | 11/2006 | Kubach | A61B 1/00057 600/118 |
| 2007/0100204 A1* | 5/2007 | Feld | A61B 1/125 600/117 |
| 2007/0149848 A1* | 6/2007 | Kubach | H04L 41/0856 600/118 |
| 2007/0238923 A1* | 10/2007 | Kubach | G01M 3/26 600/118 |
| 2017/0020367 A1* | 1/2017 | Tomita | A61B 1/00 |

FOREIGN PATENT DOCUMENTS

| | | |
|---|---|---|
| DE | 10 2008 063 273 A1 | 7/2010 |
| DE | 10 2012 020 934 A1 | 4/2014 |
| DE | 10 2012 218 754 A1 | 4/2014 |
| WO | 2016/121171 A1 | 8/2016 |

* cited by examiner

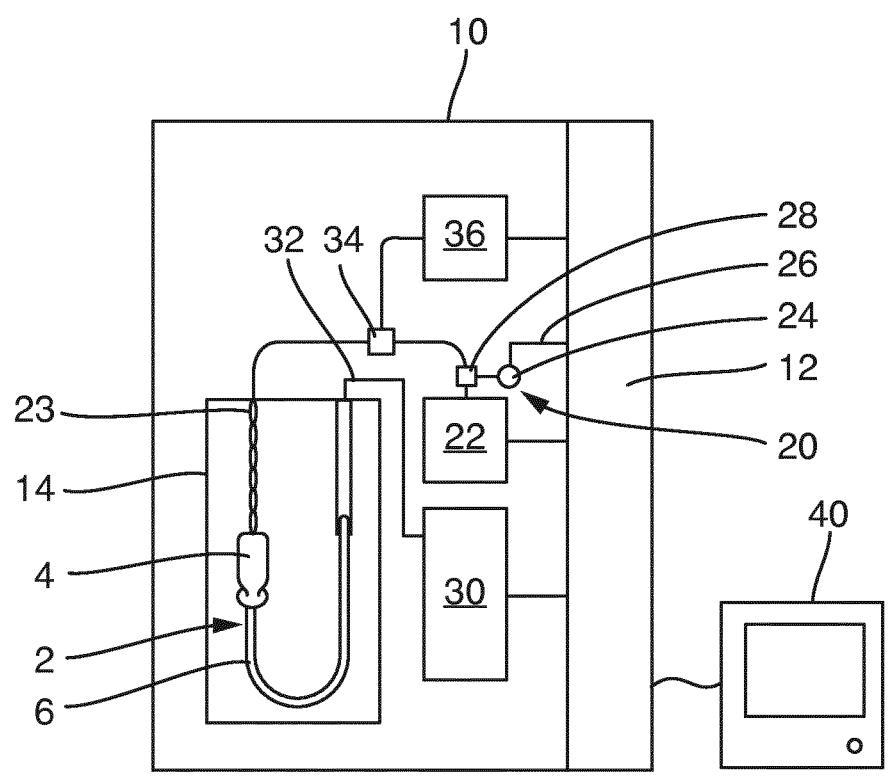

REPROCESSING SURGICAL INSTRUMENTS, IN PARTICULAR ENDOSCOPES

CROSS-REFERENCE TO RELATED APPLICATION

The present application is a continuation of PCT/EP2017/070660 filed on Aug. 15, 2017, which is based upon and claims the benefit to DE 10 2016 216 403.1 filed on Aug. 31, 2016, the entire contents of each of which are incorporated herein by reference.

BACKGROUND

Field

The present disclosure relates to a method for reprocessing a surgical instrument, in particular an endoscope, such as, a flexible endoscope in a reprocessing apparatus.

Furthermore, the present disclosure relates to a use of a drying apparatus of a reprocessing apparatus for surgical instruments, such as, endoscopes.

Prior Art

To reprocess surgical instruments, such as flexible endoscopes, normally cleaning and disinfecting devices (RDG-E) are used that are based on a chemical-thermal reprocessing procedure. In order for the endoscope to not be damaged by the cleaning liquid, it is important for the sleeve of the endoscope to be completely intact so that cleaning liquid cannot penetrate into the interior of the endoscope. This is checked in the RDG-E before the first inflow of water by pumping the endoscope up to an excess pressure via a corresponding interface. Then the drop in pressure is monitored, wherein leakage in the endoscope can be deduced from a drop in pressure. If the test fails, or respectively at the end of the procedure, i.e., at the end of the cleaning and disinfecting procedure, the endoscope is again partially ventilated. Reprocessing itself is performed at a lower excess pressure in the endoscope.

Corresponding RDG-E systems by OLYMPUS Winter & Ibe GmbH, Hamburg, are known by the designation "ETD". These systems comprise a so-called "leak tester" that performs the leak test. In so doing, an endoscope is initially pumped up to an excess pressure of, for example, 285 mbar relative to the ambient pressure after the start of the program for the leak test, and the excess pressure is reduced after the leak test to about 150 mbar above the ambient pressure. This pressure is maintained during reprocessing and monitored continuously, including to prevent the penetration of water from the outside.

When using the endoscopes in endoscopy, damage occasionally occurs in which endoscopes are punctured by biopsy channels. A microperforation arises that in certain circumstances is indiscernible in a performed leak test. During subsequent reprocessing, rinsing and clear water at a much greater pressure than 150 mbar is conducted through the channels to be rinsed. Water from rinsing the channels can thus be transferred into the region of the endoscope to be protected, which causes an increase in pressure in the endoscope above 150 mbar. The leak tester reacts to this by releasing compressed air from the endoscope to maintain the excess pressure of 150 mbar. Water can thus penetrate the tubing by way of the ventilation and ultimately enter the leak tester and, in the worst case, destroy it.

When checking the leakproofness of surgical instruments, such as endoscopes, the endoscope is connected to a leak testing device in order to check whether the outer sleeve of the endoscope and the channels of the endoscope are completely intact.

Before the initial cleaning process with a liquid, such as water, a check is automatically performed by connecting the leak testing device to the endoscope via a corresponding port, and then pumping the endoscope up to an overpressure. Then the drop in pressure is monitored in order to identify leakage in the endoscope.

Due to the interface that for example flexible endoscopes have for checking the leak of the endoscope sleeve and ventilating the endoscope, there is the risk of water penetrating the intact endoscope sleeve from improper handling by a user. Moreover, leaks can arise in the endoscope channels that are not discerned at the low test pressure in the context of the leak test (about 300 mbar); however, at the higher rinsing pressures (about 1300 mbar), they allow water to penetrate into the endoscope sleeve, whereby the excess pressure in the endoscope sleeve (approximately 150 mbar) also cannot be prevented. This can cause the endoscope to be damaged.

To the extent that there is water in a leaky endoscope, this can cause the penetrated water to be able to enter into the cleaning and disinfecting device (RDG-E) during ventilation, which also damages it.

To identify leakiness, the endoscope is brought to a test pressure, typically 275 mbar to 300 mbar, before performing the endoscope cleaning process, and then it is tested for a specific period of time such as 60 seconds. If the pressure within the endoscope decreases by more than a predetermined amount, typically between 10 mbar to 15 mbar, the endoscope is considered leaky, and subsequent reprocessing is therefore not performed.

Moreover, in current leak test methods, an imprecision exists of reliably identifying certain types of leaks, especially direction-dependent leaks.

SUMMARY

In light of this prior art, an object is to improve the leak test, such as, when performing an automated leak test in a reprocessing apparatus.

Such object can be achieved with a method for reprocessing a surgical instrument, such as, an endoscope, and a flexible endoscope, in a reprocessing apparatus, wherein the surgical instrument has at least one channel to be cleaned or rinsed, such as, a working channel, and the surgical instrument is airtightly connected to a compressed air hose and compressed air for the leak test, wherein drying air is applied to the compressed air hose from a drying apparatus of the reprocessing apparatus prior to reprocessing the surgical instrument using at least one cleaning liquid such that the surgical instrument leak test is performed by the utilized drying air.

Such method configures a reprocessing apparatus for cleaning and/or disinfecting surgical instruments, such as, endoscopes with a drying apparatus for drying the channels, such as, working channels, of the surgical instrument, or respectively endoscope, wherein the drying apparatus is used, or respectively employed, for the initiated leak test of the surgical instrument, or respectively endoscope, such that the automated leak test uses the drying air of the drying apparatus in the reprocessing apparatus.

The drying apparatus provides the drying air. Drying air is dried and is dryer in comparison to conventional compressed air, and accordingly has less moisture. It can be provided that the drying apparatus provides hot or heated dry air. The drying apparatus can have a filter or the like in which the moisture withdrawn from the air is absorbed. The drying apparatus is to be distinguished from a compressed air source. A compressed air source serves to provide compressed air, i.e., air that has not passed through a drying process.

In this regard, when the leak test is being performed, drying air is applied to the channel to be cleaned or rinsed, such as, the working channel, wherein the drying air is guided through the channel. If a leak occurs in the working channel, or respectively inner channel, this would cause a pressure rise in a protected region of the surgical instrument so that it is determined that the surgical instrument is leaky using the detected pressure rise in the region that is protected from the channel.

The reprocessing apparatus with the drying apparatus can be a cleaning and disinfection device (RDG-E).

The drying air can be applied to the surgical instrument by a compressed air pulse with a duration of less than 20 seconds, such as, between 1 second to 15 seconds. To test the leakproofness using the compressed air pulse, the drying apparatus can be briefly activated in order to determine any leakiness of the surgical instrument.

Moreover, the drying air can be applied to the surgical instrument at a pressure greater than 500 mbar, such as, greater than 800 mbar, or greater than 1000 mbar. For this, a pressure can be applied to the surgical instrument greater than 500 mbar, or 600 mbar, or 700 mbar, or 800 mbar, or 900 mbar, or 1000 mbar, or 1100 mbar, or 1200 mbar.

The surgical instrument can have a region that is protected from the channel, such as, a shaft region of the surgical instrument, or an endoscope shaft region, in addition to the at least one channel, such as, the working channel, wherein after drying air is applied to the channel of the surgical instrument, a leak in the surgical instrument can be determined when a predetermined pressure setpoint of the protected region is exceeded. Since the pressure of the drying air used for the leakproofness test can be higher than the water pressure used for cleaning, the leakage of the surgical instrument can be determined when a predetermined pressure setpoint for the region of the surgical instrument protected from the channel is exceeded.

Overall, this significantly increases the reliability of identifying leaks since the leaks are reliably identified before reprocessing the surgical instrument in the reprocessing apparatus. Since, in the method, the pressure differential can be higher than in the method known in the prior art, the operational safety of the reprocessing apparatus can be significantly increased.

In this regard, one embodiment moreover provides that after the leak in the surgical instrument is determined, the additional reprocessing process for the surgical instrument can be stopped.

The reprocessing of the surgical instrument can be continued when a or the predetermined pressure setpoint for the protected region of the surgical instrument is undershot.

Moreover, such object can be achieved by using a drying apparatus of a reprocessing apparatus for surgical instruments, such as, endoscopes, to perform the above-described method for reprocessing a surgical instrument, such as, a flexible endoscope. We expressly refer to the above explanations in order to avoid repetitions.

Further features will become apparent from the description of embodiments together with the claims and the attached drawing. Embodiments can fulfill individual features or a combination of several features.

BRIEF DESCRIPTION OF THE DRAWINGS

The embodiments are described below, without restricting the general idea of the invention, based on an exemplary embodiment in reference to the FIGURE, whereby express reference is made to the FIGURE with regard to the disclosure of all details that are not explained in greater detail in the text. In the FIGURES:

The FIGURE illustrates a schematic representation of a cleaning and disinfecting device.

DETAILED DESCRIPTION

The FIGURE shows a schematic representation of a reprocessing system 10 with a cleaning chamber 14 in which a flexible endoscope 2 is arranged that is ready to be cleaned and disinfected. The endoscope 2 comprises a handle 4 as well as a flexible shaft 6 which are both connected to connections of the reprocessing system 10.

The shaft 6 of the endoscope 2 is connected via a port to a reprocessing apparatus 30 of the reprocessing system 10, whereas the handle 4 is connected via a compressed air hose 23 with a compressed air source 22, such as a compressor, to the apparatus 20 for applying compressed air, termed a "leakage tester" for short. Like the reprocessing apparatus 30, this is connected to a controller 12 of the reprocessing system 10, which accordingly also represents a controller for the apparatus 20 for applying compressed air. The compressed air source 22 serves to provide compressed air.

At the outlet of the compressed air source 22, an air compressor sensor 24 is connected to the compressed air hose 23 that measures the excess pressure of the air in the compressed air hose 23 above the ambient pressure, and also transmits corresponding signals via a signal line 26 to the controller 12 of the reprocessing system 10. The controller 12 is moreover connected to a display apparatus 40 by means of which the controller 12 can be influenced externally, and conversely, data from the controller 12 can be displayed, such as measured excess pressure data from the air pressure sensor 24 and/or process data.

The apparatus 20 for applying compressed air is connected to the compressed air source 22 via the compressed air hose 23 to the endoscope 2, which is only schematically indicated, whereby compressed air is pumped into the endoscope 2 via a valve 28 and a valve 34 switched to open position, and then is also released again.

The air pressure sensor 24 is connected to the compressed air hose 23 and measures the pressure of the compressed air in the compressed air hose 23 and in the endoscope 2. The air pressure sensor 24 can alternatively also measure directly at the endoscope 2 or at the outlet of the compressed air source 22.

Furthermore, the reprocessing system 10 has a drying apparatus 36 that is provided and set up to apply drying air to the channel(s) of the endoscope 2 after the rinsing and/or disinfection processes that are performed after a leak test of the endoscope 2 has been passed, and to dry the channel(s) of the endoscope 2. The drying apparatus 36 serves to provide drying air. Drying air has reduced moisture; in this regard, the drying apparatus 36 is for example equipped with a filter that absorbs moisture. In comparison to conventional compressed air that for example is provided by the compressed air source 22, the drying air provided by the drying apparatus 36 is air with less moisture.

Moreover, the drying apparatus 36 is used before performing the rinsing and/or disinfection processes in order to apply drying air to the endoscope, or respectively the channel(s) of the endoscope 2, when performing the initial leak test. In so doing, the drying air is conducted from the drying apparatus 36 via the valve 34 into the compressed air hose 32. In so doing, a pressure greater than 800 mbar or 1000 mbar or more is for example applied to the drying air. The drying air in so doing can be conducted by means of a pulse, such as, with a pulse duration of one second to 15 seconds, into the endoscope 2, or respectively its channel(s). Then, the valve 36 is configured such that the drying air is conducted via the compressed air hose 23 into the compressed air sensor 24 for the leak test.

In so doing, the pressure, or respectively air pressure can be detected in a region protected from a rinsing channel by a casing. If it is determined by means of the compressed air sensor 24 that a predetermined setpoint has been exceeded after applying compressed air to the endoscope 2, it is determined by means of the controller 12 that a leak in the endoscope 2 exists. In this case, the reprocessing process in the reprocessing system 10 is stopped.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE NUMBER LIST

2 Endoscope
4 Handle
6 Flexible shaft
10 Reprocessing system
12 Control unit
14 Cleaning chamber
20 Apparatus for applying compressed air
22 Compressed air source
23 Compressed air hose
24 Air pressure sensor
26 Signal line
28 Valve
30 Reprocessing apparatus
32 Rinsing hose
34 Valve
36 Drying apparatus
40 Display unit

What is claimed is:

1. A method for reprocessing a surgical instrument in a reprocessing apparatus, wherein the surgical instrument has at least one channel to be cleaned, the reprocessing device having a drying apparatus for providing drying air to the at least one channel and a compressed air source for providing compressed air to the at least one channel, the compressed air from the compressed air source being provided separately from the drying air from the drying apparatus, the method comprising:
   connecting the at least one channel to a compressed air hose;
   supplying compressed air from the compressed air source to the at least one channel via the compressed air hose;
   supplying drying air from the drying apparatus to the at least one channel via the compressed air hose to leak test the surgical instrument using the drying air, the drying air having a moisture content lower than a moisture content of the compressed air; and
   while the at least one channel remains connected to the compressed air hose and subsequent to the supplying of the drying air, reprocessing the surgical instrument to clean the at least one channel using at least one cleaning liquid;
   wherein the surgical instrument has a protected region that is protected from the at least one channel, wherein subsequent to supplying the drying air to the channel, the method further comprises determining a leak in the surgical instrument when a predetermined pressure setpoint of the protected region is exceeded; and
   the pressure of the drying air used in the leak test is higher than a pressure used in the reprocessing.

2. The method according to claim 1, wherein the supplying of the drying air comprises pulsing the drying air with a duration of less than 20 seconds.

3. The method according to claim 2, wherein the duration is between 1 and 15 seconds.

4. The method according to claim 1, wherein the supplying of the drying air comprises supplying the drying air at a pressure greater than 500 mbar.

5. The method according to claim 4, wherein the pressure is greater than 800 mbar.

6. The method according to claim 4, wherein the pressure is greater than 1000 mbar.

7. The method according to claim 1, wherein, where a leak is determined in the surgical instrument, the method further comprises stopping the reprocessing.

8. The method according to claim 1, wherein, when a leak is not determined, the method comprises continuing the reprocessing.

* * * * *